United States Patent [19]

Burton-Krahn et al.

[11] Patent Number: 5,758,654
[45] Date of Patent: Jun. 2, 1998

[54] ECG P QRS T ONSET AND PEAK DETECTION METHOD

[75] Inventors: Noel Morgen Burton-Krahn; Reinhard Illner; Robert Clifford Bruce Steacy, all of Victoria, Canada

[73] Assignee: Harley Street Software Ltd., Victoria, Canada

[21] Appl. No.: 846,348

[22] Filed: Apr. 30, 1997

Related U.S. Application Data

[63] Continuation-in-part of Ser. No. 705,621, Aug. 29, 1996, abandoned.

[51] Int. Cl.$^6$ ............................................. A61B 5/0452
[52] U.S. Cl. ............................................. 128/704
[58] Field of Search ......................... 128/696, 702–704, 128/708

[56] References Cited

U.S. PATENT DOCUMENTS

| | | | |
|---|---|---|---|
| 4,240,442 | 12/1980 | Andresen et al. | 128/708 |
| 4,704,681 | 11/1987 | Shimuzu et al. | 128/704 |
| 4,793,361 | 12/1988 | DuFault | 128/696 |
| 4,945,917 | 8/1990 | Akselrod et al. | 128/696 |
| 5,092,341 | 3/1992 | Kelen | 128/702 |
| 5,148,812 | 9/1992 | Verrier et al. | 128/704 |
| 5,224,486 | 7/1993 | Lerman et al. | 128/696 |
| 5,469,858 | 11/1995 | Osborne | 128/710 |

OTHER PUBLICATIONS

Laguna, et al.; "Automatic Detection of Wave Boundaries on Multilead ECG Signals: Validation with the CSE Database"; Computers and Biomedical Research, vol. 27, pp. 45–60; 1994.

Pan, J. and Thompkins, W. J.; "A Real–Time QRS detection Algorithm" IEEE Transactions on Biomedical. Engineering., vol. 32, pp. 230–236; 1985.

Reddy, et al; "Detection of P Waves in Resting ECG: A Preliminary Study"; IEEE; 1992.

Koski, et al; "Syntactic Recognition of ECG Signals by Attributed Finite Automata"; 1995.

Brooks, et al; "Best Basis Segmentation of ECH Signals Using Novel Optimality Criteria"; Proc. ICASSP 1996. Atlanta, GA, May, 1996.

Okada; "A Digital Filter for the QRS Complex Detection"; IEEE Transactions on Biomedicald. Engineering., vol. 26, pp. 700–703; 1979.

Pretorius, et al; "Feature Extraction From ECG For Classification By Articficial Neural Networks"; Fifth Annual IEEE symposium on Computer–Based Medical Systems; pp. 639–647; 1992.

*Primary Examiner*—Jeffrey R. Jastrzab
*Attorney, Agent, or Firm*—Oyen Wiggs Green & Mutala

[57] ABSTRACT

A method and apparatus for detecting P or T waves in an electrocardiogram signal in intervals before and after each (previously) detected QRS wave. Within each interval, a candidate pair of samples are selected. If the candidate pair are separated by a time duration which does not exceed a predefined time duration then that pair is rejected and the process repeats. Otherwise, the area "A" of a closed polygon bounded by all of the samples between and including the candidate pair is derived (the polygon's base line extends linearly a distance "d" between the candidate pair of sample intervals). The maximum vertical displacement "h" between the base line and any portion of the polygon above the base line is derived. If "h" does not exceed a predefined minimum vertical displacement, then the candidate pair is rejected and the process repeats. Otherwise, a value Gamma=A*h/d is derived for the candidate pair. If Gamma does not exceed any value of Gamma derived previously in respect of any previously selected candidate pair, then the candidate pair is rejected and the process repeats. Otherwise, a value Best-Gamma is set equal to the candidate pair's value Gamma. Another candidate pair is then selected and the process repeats. The P or T wave is selected as that whose value Gamma equals the value BestGamma.

6 Claims, 10 Drawing Sheets

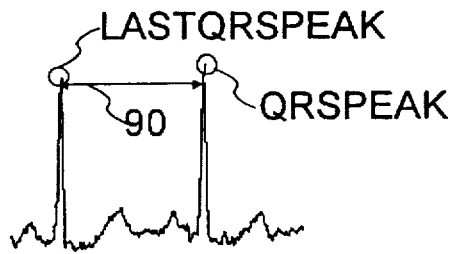
FIG. 9D
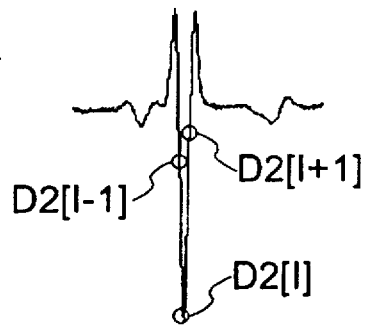
FIG. 9E
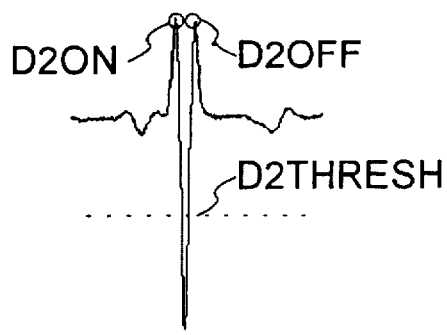
FIG. 9F
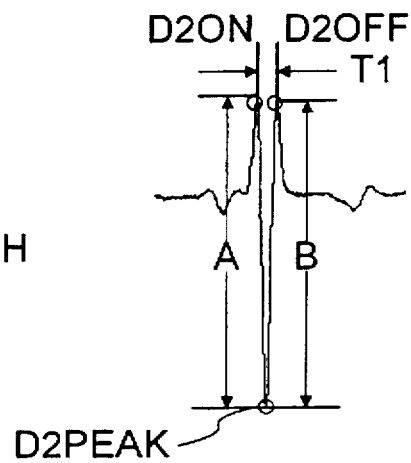
FIG. 9G
FIG. 9H
FIG. 9I

ECG P QRS T ONSET AND PEAK DETECTION METHOD

REFERENCE TO RELATED APPLICATION

This is a continuation-in-part of United States application Ser. No. 08/705,621 filed 29 Aug., 1996 now abandoned.

FIELD OF THE INVENTION

This application pertains to identification of P, T and QRS waves in electrocardiogram ("ECG") signals.

BACKGROUND OF THE INVENTION

ECG signals are obtained by applying adhesive patch or metal plate electrodes to a patient's chest and connecting the electrodes to a cardiograph machine. The cardiograph measures voltage differences between pairs of electrodes. The voltage difference between each pair of electrodes is a "lead". The cardiograph sequentially measures the leads at regular time intervals and stores the measurements. A sequence of such measurements is referred to as set of "ECG samples". The "sampling rates' is the frequency at which the measurements are made. Sampling rates of 125, 250, 500, or 1000 samples per second are typical. Typical ranges for the measurements are −5 mV to +5 mV, divided into $2^8$, $2^{12}$, or $2^{16}$ measurement intervals.

FIG. 1 depicts a typical ECG signal consisting of several heart beat segments. Each beat of a patient's heart produces a unique ECG signal segment, such as the single heart beat cycle ECG signal segment shown in FIG. 2. According to well known principles of cardiology, each heart beat cycle typically includes a "P" wave 10, a "QRS" wave 12 and a "T" wave 14. Each of these waves is representative of a particular characteristic of the patient's heart beat.

Each P, QRS, and T wave begins at a specific "onset" and ends at a specific "offset". Each wave also has a "peak", which is the wave's maximum displacement relative to a predefined "baseline". However, electrodes placed in different locations on the same patient yield different ECG signals in response to the same heart beat. Accordingly, variations from lead to lead in the onset, offset, and peak values for each P, QRS, and T wave are common. For some leads in some ECG signals, a P, QRS or T wave may not be evident at all.

The aforementioned "baseline" is the electrical signal measured by the cardiograph in the absence of cardiac activity. The baseline is not flat, but wanders up and down as the patient's body moves. Accordingly, P, QRS and T waves are not seen relative to a flat horizontal line, but relative to a wandering baseline, as shown in FIG. 3. Variations in ECG signal measurements can also result from noise introduced by movement of the patient's body, electromagnetic interference, etc. For example, patient muscle activity can introduce high frequency noise as shown in FIG. 4. Such noise can be of the same amplitude as the P or T waves, and must be removed for accurate measurement of P or T waves.

Various prior art techniques have been devised to detect P, QRS, or T waves in ECG signals. For example, Pan et al use a moving window integrator to detect QRS waves, but make no attempt to detect P or T waves (see Pan, J. and Thompkins, W. J.; "A Real-Time QRS detection Algorithm", IEEE Transactions on Biomedical Engineering, vol. 32, pp. 230–236, 1985).

Reddy, et al use a derivative and threshold technique to detect P waves (see Reddy, et. al; "Detection of P Waves in Resting ECG: A Preliminary Study"; IEEE, 1992). However, because derivatives are affected both by baseline wander and by noise, this technique is susceptible to error in the presence of either baseline wander or noise, both of which are common.

Laguna, et al use the signal slope to identify the QRS wave, use derivatives to find the peaks of the P and T waves, and use derivatives and thresholding to find the onsets and offsets of the P and T waves (see Laguna, et al.; "Automatic Detection of Wave Boundaries on Multilead ECG Signals: Validation with the CSE Database"; Computers and Biomedical Research, vol. 27, pp. 45–60, 1994). This method is also error-prone in the presence of baseline wander or noise.

Koski, et al. use syntactic methods based on signal slope to identify P, QRS, and T waves (see Koski, et al; "Syntactic Recognition of ECG Signals by Attributed Finite Automata"; 1995). This method is also believed to be error-prone in the presence of baseline wander or noise.

U.S. Pat. No. 4,945,917 Akselrod, et al discloses a technique for detecting fetal QRS waves in which maternal QRS waves are first detected in an operator-assisted "learning" phase by deriving first and second derivatives of a portion of the maternal ECG signal. A "template" representative of the maternal QRS wave is then constructed and subtracted from a composite maternal-fetal ECG signal to derive the fetal QRS wave. This technique is subject to a number of disadvantages, including the need for operator intervention, and reliance upon a fixed template which may be a poor representation of the continuously variable QRS wave as the patient's heart beat conditions vary.

U.S. Pat. No. 4,704,681 Shimuzu, et al discloses an apparatus for detecting certain "delta waves" within previously detected QRS waves. No provision is made for detecting P or T waves.

The present invention provides a method and apparatus for reliably, automatically detecting P, QRS and T waves in high speed processing of large volumes of ECG signal data representative of multiple leads and many heart beat cycles.

SUMMARY OF THE INVENTION

The invention provides a method and apparatus for detecting P or T waves in an electrocardiogram signal in intervals before and after each (previously) detected QRS wave. Within each interval, a candidate pair of samples are selected. If the candidate pair are separated by a time duration which does not exceed a predefined time duration then that pair is rejected and the process repeats. Otherwise, the area "A" of a closed polygon bounded by all of the samples between and including the candidate pair is derived (the polygon's base line extends linearly a distance "d" between the candidate pair of samples). The maximum vertical displacement "h" between the base line and any portion of the polygon above the base line is derived. If "h" does not exceed a predefined minimum vertical displacement, then the candidate pair is rejected and the process repeats. Otherwise, a value Gamma =A*h/d is derived for the candidate pair. If Gamma does not exceed any value of Gamma derived previously in respect of any previously selected candidate pair, then the candidate pair is rejected and the process repeats. Otherwise, a value Best-Gamma is set equal to the candidate pair's value Gamma. Another candidate pair is then selected and the process repeats. The P or T wave is selected as that whose value Gamma equals the value BestGamma.

DETAILED DESCRIPTION OF THE PREFERRED EMBODIMENT

Introduction

Figure 1:
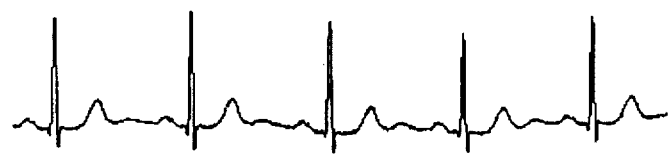
FIG. 1 depicts a typical ECG signal consisting of several heart beat cycle segments.
Figure 2:
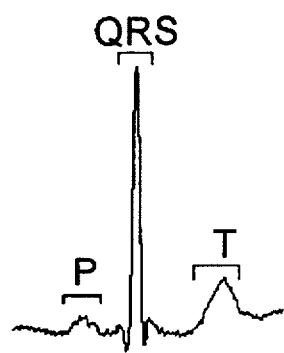
FIG. 2 depicts a single heart beat cycle segment of the FIG. 1 ECG signal.
Figures 3, 4:
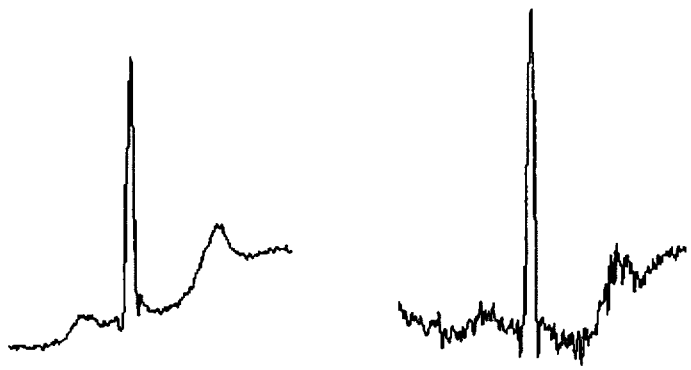
FIG. 3 depicts a single heart beat cycle segment of the FIG. 1 ECG signal in which the ECG baseline is wandering.
FIG. 4 depicts a single heart beat cycle segment of the FIG. 1 ECG signal in which the signal is contaminated by high frequency noise.
Figure 5:
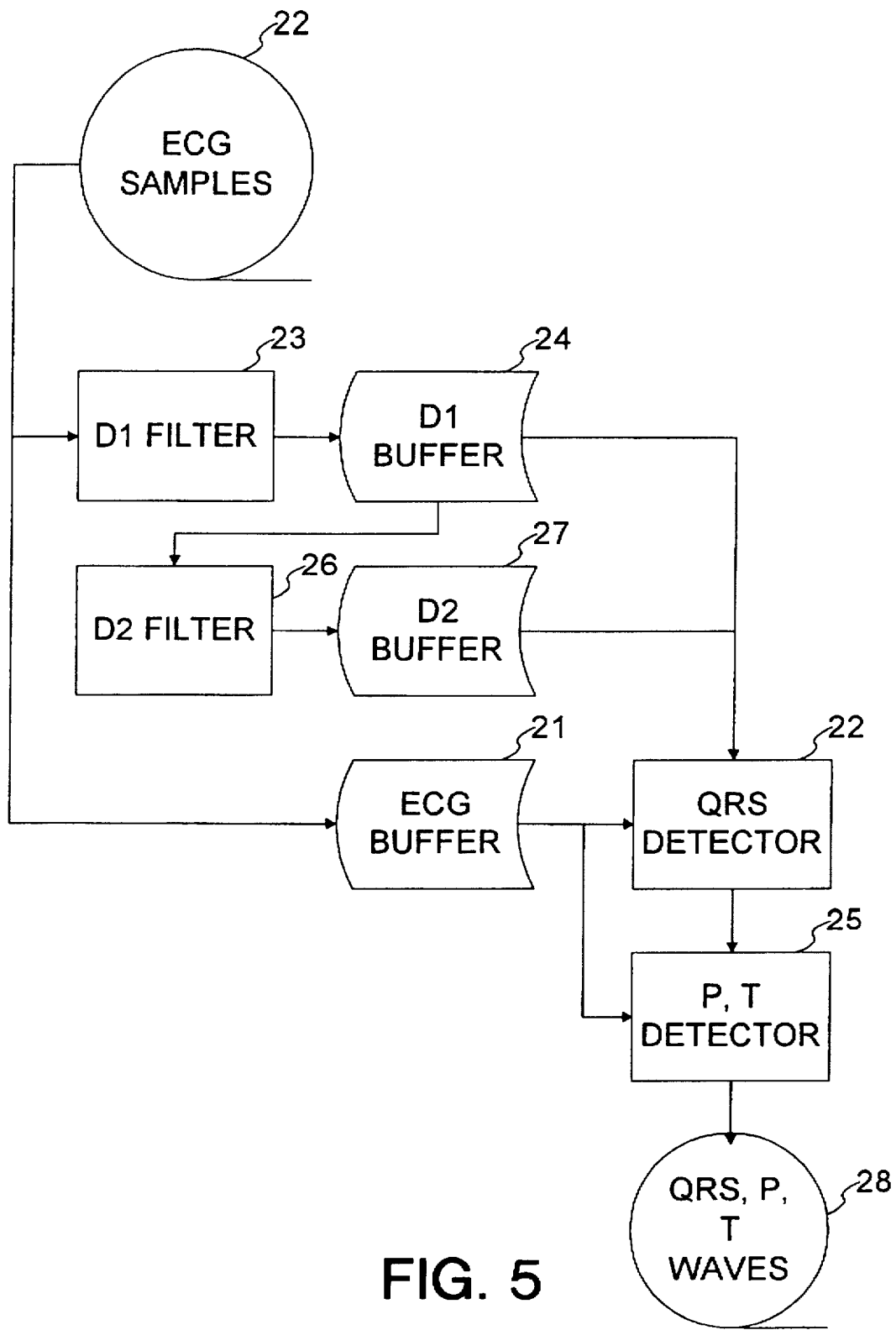
FIG. 5 is a block diagram of a P, QRS, and T wave detector according to the invention.

FIG. 5 is a block diagram representation of an apparatus for processing previously measured and stored ECG samples 20 in accordance with the invention. Each ECG sample waveform is generally of the form shown in FIG. 9A, which is identical to the previously discussed FIG. 2 waveform. Buffer 21 stores a selected group of ECG samples while approximations to the first and second derivatives of those samples are derived.

Figure 9A:
FIGS. 9A through 9S are signal waveforms which respectively depict successive stages of the operation of the preferred embodiment of the invention.
Figure 9B:
Figure 9C:
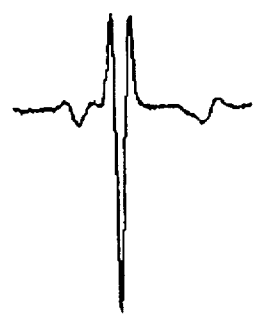

Specifically, filter 23 receives the FIG. 9A ECG sample waveform as input, and produces as output a signal representative of the first derivative ("D1") thereof, as shown in FIG. 9B. Filter 26 also receives the FIG. 9A ECG sample waveform as input, and produces as output a signal representative of the second derivative ("D2") thereof, as shown in FIG. 9C. Buffer 24 stores the first derivative representations output by filter 23, and buffer 27 stores the second derivative representations output by filter 26.

Figure 6A:
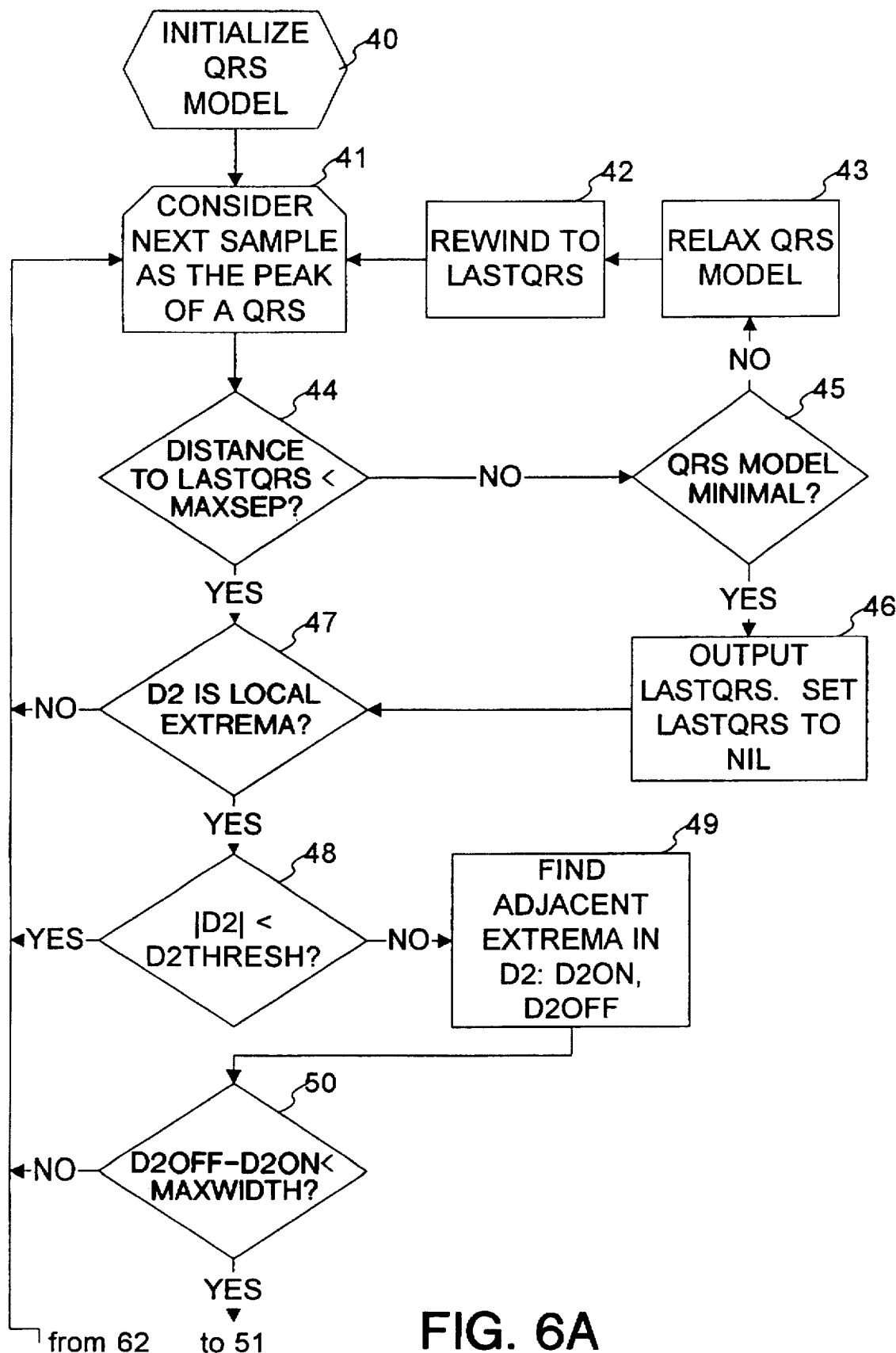
FIGS. 6A and 6B together comprise a flowchart which depicts the sequence of steps performed in detecting QRS waves in accordance with the invention.
Figure 6B:
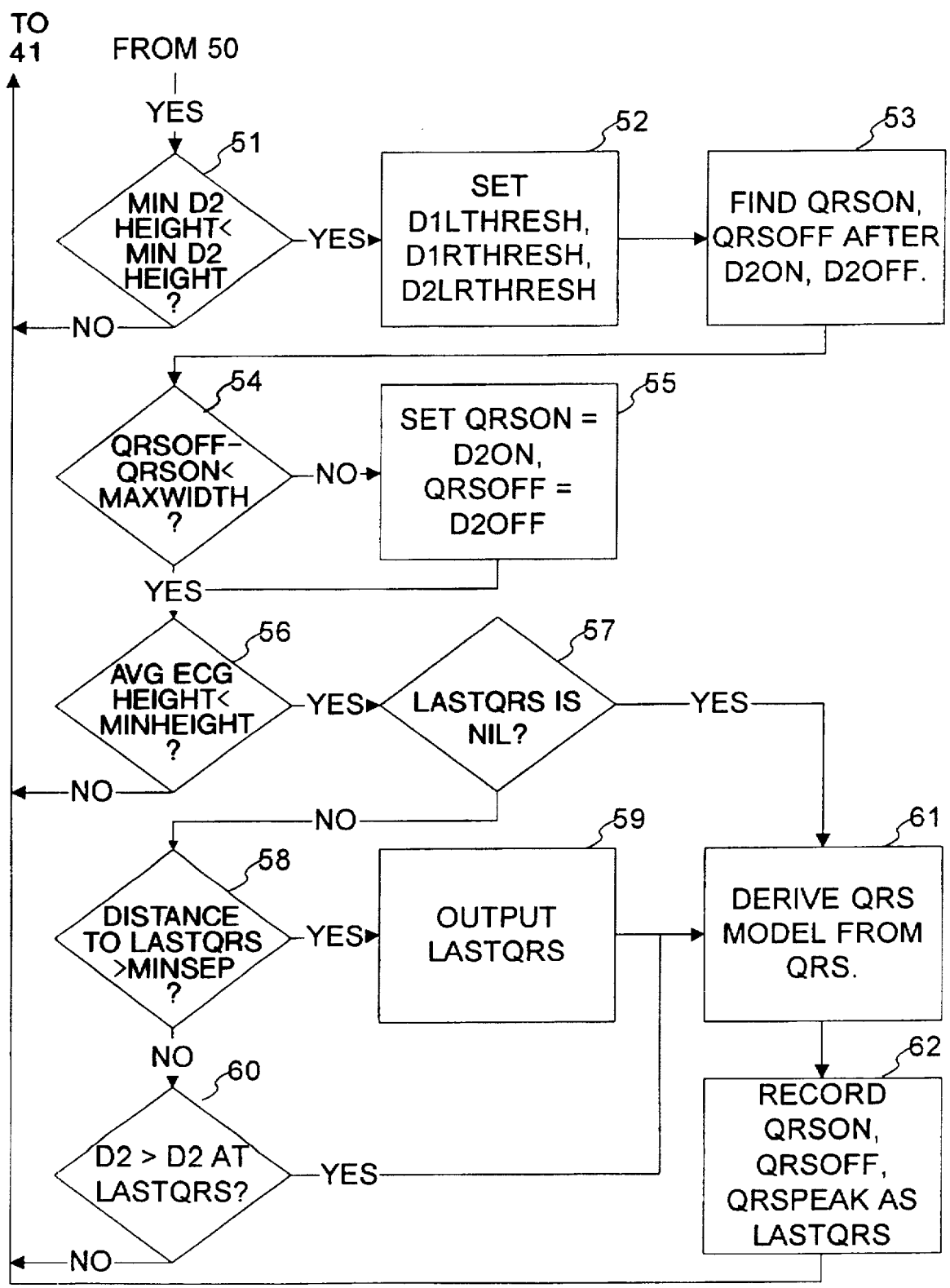

As hereinafter described in greater detail, QRS detector 22 applies the algorithm depicted in FIGS. 6A and 6B to the ECG samples stored in buffer 21, to the first derivative representations stored in buffer 24 and to the second derivative representations stored in buffer 27 to detect the onsets, peaks, and offsets of QRS waves in each ECG sample waveform. P and T wave detector 25 applies the algorithm depicted in FIG. 7 to the output of QRS detector 22 and to the ECG samples stored in buffer 21 to detect the onsets, peaks, and offsets of the P and T waves in each ECG sample waveform. The onsets, offsets, and peaks of the P, QRS, and T waves output by QRS detector 22 and by P and T detector 25 are stored as a sequential record 28, which can be on a computer disk, tape, memory, or communications channel.

QRS Wave Detection

The operation of QRS detector 22 will now be described with reference to FIGS. 6A and 6B. Such operation is conveniently characterized in terms of the following definitions:

MaxQRSSep absolute maximum distance between QRS waves

MaxSep maximum distance between QRS waves

MinQRSSep absolute minimum distance between QRS waves

MinSep minimum distance between QRS waves

MinQRSWidth absolute minimum time between QRS wave onset and offset

MaxQRSWidth absolute maximum time between QRS wave onset and offset

MinQRSHeight absolute minimum height from onset or offset to peak

MaxWidth maximum time between QRS wave onset and offset

MinWidth minimum time between QRS wave onset and offset

MinHeight minimum height from onset or offset to peak

D2Thresh minimum value of second derivative at QRS peak

MinD2Height minimum height from onset or offset to peak in second derivative

QRSPeak peak of current candidate QRS wave

QRSOn onset of current candidate QRS wave

QRSOff offset of current candidate QRS wave

LastQRSPeak peak of previously detected QRS wave

LastQRSOn onset of previously detected QRS wave

LastQRSOff offset of previously detected QRS wave

An initialization step 40 is first performed to set the following initial values:

MaxQRSSep := 2 seconds
MaxSep := MaxQRSSep
MinQRSSep := 0.2 seconds
MinSep := MinQRSSep
MinQRSWidth := 25 milliseconds
MaxQRSWidth := 240 milliseconds
MinQRSHeight := 0.25mV
MaxWidth := MaxQRSWidth
MinWidth := MinQRSWidth
MinHeight := MinQRSHeight
D2Thresh := 0
MinD2Height := 0
D1Lthresh := 0
D1Rthresh := 0
D2LRThresh := 0
LastQRSPeak := nil
LastQRSOn := nil
LastQRSOff := nil At step 41, the next ECG sample is retrieved from buffer 21, and that sample (called "QRSPeak") is evaluated to determine whether a QRS wave can be detected therein. Step 41 is the first step in a loop. QRSPeak is incremented by one with each repetition of step 41. At step 44, a test is performed to determine whether the distance 90 (FIG. 9D) between the peak of the current candidate QRS wave (i.e. QRSPeak) and the peak of the previously detected QRS wave (i.e. LastQRSPeak) is less than the maximum distance between QRS waves (i.e. MaxSep), or whether LastQRSPeak is nil (as it will be if the current candidate QRS wave is the first sample processed from buffer 21).

If distance 90 is not less than MaxSep, or if LastQRSPeak is nil, then a further test step 45 is performed to determine whether threshold values D2Thresh, MinD2Height, MinHeight and MinWidth are minimal. These threshold values are minimal if the following conditions are met:

D2Thresh $\leq$ 0
MinD2Height $\leq$ 0
MinHeights $\leq$ MinQRSHeight
MinWidths $\leq$ MinQRSWidth If the threshold values D2Thresh, MinD2Height, MinHeight and MinWidth are not minimal, then step 43 is performed to relax those threshold values, as well as the threshold values MaxSep, MinSep, MaxWidth by resetting their respective values as follows:

MaxSep := Min(MaxQRSSep, MaxSep*2)
MinSep := Max(MinQRSSep, MinSep/2)
MaxWidth := MIN(MaxQRSWidth, MaxWidth*2)
MinWidth := MAX(MinQRSWidth, MinWidth/2)
MinHeight := MAX(MinQRSHeight, MinHeight/2)
D2Thresh := 2
MinD2Height := 2

After relaxation step 43, step 42 is performed to reset the previously detected QRS wave (i.e. LastQRSPeak) as the sample to be evaluated, commencing with step 41, to determine whether a QRS wave can be detected therein. Accordingly, the candidate QRS wave which was unsuccessfully processed during the previously described steps will again be processed, with different threshold values, to determine whether a QRS wave can be detected therein. If test step 45 determines that threshold values D2Thresh, MinD2Height, MinHeight and MinWidth are minimal, then step 46 is performed to output the last QRS and to set LastQRSPeak to nil.

At this point, QRS detector 22 has reached a stage at which the QRS wave following an earlier-detected QRS wave can not be detected. A detected QRS wave is not immediately output, because it may be invalidated by a subsequently detected QRS wave. If no following QRS wave is detected, then the last detected QRS wave is accepted as valid and its onset, offset and peak values are output. Once a QRS wave is output, it need not be retained in memory. Since no new QRS wave has been detected, LastQRSPeak is set to nil.

After performance of step 46; or, if test step 44 determines that distance 90 is less than MaxSep, and that LastQRSPeak is not nil, then a further test step 47 is performed on the second derivative representation (input to QRS detector 22 from buffer 27) of the ECG sample currently being processed by QRS detector 22. As depicted in FIG. 9E, test step 47 determines whether the second derivative at QRSPeak is a local extrema. If the ECG sample currently being processed by QRS detector 22 is sample "i", then its second derivative is a local extrema if and only if $D2[i-1] \leq D2[i] \geq D2[i+1]$; or, $D2[i-1] \geq D2[i] \leq D2[i+1]$.

If test step 47 determines that the second derivative at QRSPeak is not a local extrema, then the loop is repeated commencing with step 41. Otherwise, if test step 47 determines that the second derivative at QRSPeak is a local extrema, then a further test step 48 is performed to determine whether the absolute value of the second derivative at QRSPeak is less than D2Thresh, as shown in FIG. 9F. If test step 48 determines that the absolute value of the second derivative at QRSPeak is less than D2Thresh, then the loop is repeated commencing with step 41. Otherwise, if test step 48 determines that the absolute value of the second derivative at QRSPeak is less than D2Thresh, step 49 is performed to set indices D2On, D2Off (FIG. 9F) equal to the indices of the local extrema adjacent QRSPeak in the second derivative of the ECG sample currently being processed by QRS detector 22.

After performance of step 49, a further test step 50 is performed to determine whether the time "t1" (FIG. 9G) between D2Off and D2On is less than MaxWidth. If test step 50 determines that the time between D2Off and D2On is not less than MaxWidth, then the loop is repeated commencing with step 41. Otherwise, if test step 50 determines that the time between D2Off and D2On is less than MaxWidth, then a further test step 51 is performed to determine whether the minimum difference in the values "a", "b" (FIG. 9G) of the second derivative between D2On and D2Peak or between D2Off and D2Peak are less the MinD2Height.

If test step 51 determines that the minimum difference in the values of the second derivative between D2On and D2Peak; or, between D2Off and D2Peak are not less the MinD2Height, then the loop is repeated commencing with step 41. Otherwise, if test step 51 determines that the minimum difference in the values of the second derivative between D2On and D2Peak; or, between D2Off and D2Peak are less the MinD2Height then step 52 is performed to set threshold values D1LThresh, D1RTthresh for the first derivative, and to set threshold value D2LRThresh for the second derivative between D2On and D2Off, as shown in FIG. 9H. More particularly, the threshold values are set as follows:

D1LThresh := ¼ the maximum value in the first derivative between D2On and QRSPeak D1RThresh := ¼ the maximum value in the first derivative between QRSPeak and D2Off D2LRThresh := ¼ the maximum value in the second derivative between D2On and D2Off After performance of step 52, step 53 is performed, as depicted in FIG. 9I, to set QRSOn and QRSOff to the indices near QRSPeak where the values of the first and second derivatives are below D1Lthresh and D2LRThresh for QRSOn, and below D1RThresh and D2LRThresh for QRSOff.

Figure 9J:
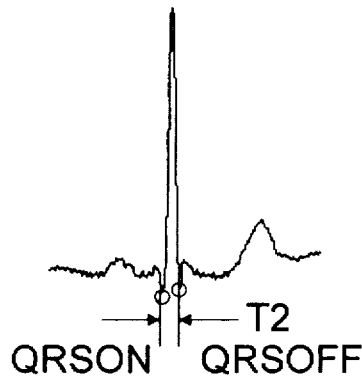
Figure 9K:
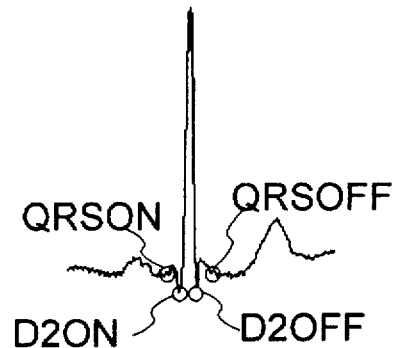
Figure 9L:
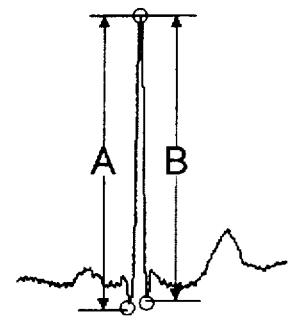

After performance of step 53, test step 54 is performed to determine whether the time "t2" (FIG. 9J) between QRSOn and QRSOff is less than MaxWidth. If test step 54 determines that the time between QRSOn and QRSOff is not less than MaxWidth, then step 55 is performed to set QRSOn and QRSOff equal to D2On and D2Off respectively (FIG. 9K). If test step 54 determines that the time between QRSOn and QRSOff is less than MaxWidth; or, after performance of step 55 if needed, test step 56 is performed to determine whether the average height difference from QRSOn to QRSPeak (i.e. distance "a" in FIG. 9L); and, from QRSOff to QRSPeak (i.e. distance "b" in FIG. 9L) is less than MinHeight. If test step 56 determines that the average height difference aforesaid is not less than MinHeight, then the loop is repeated commencing with step 41.

Figure 9M:
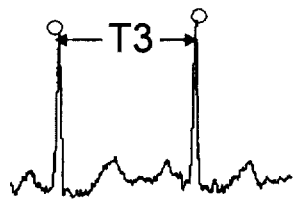
Figure 9N:
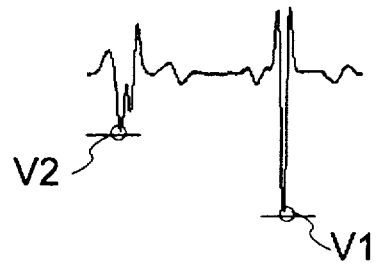

Otherwise, if test step 56 determines that the average height difference aforesaid is less than MinHeight then a test step 57 is performed to determine whether LastQRSPeak is nil (i.e. to determine whether LastQRSPeak has been accepted as a QRS wave). If test step 57 determines that LastQRSPeak is not nil, then a further test step 58 is performed to determine whether the time "t3" (FIG. 9M) between LastQRSPeak and QRSPeak is greater than MinSep. If test step 58 determines that the time between LastQRSPeak and QRSPeak is greater than MinSep, then LastQRSPeak is accepted as a valid QRS wave and is as such at step 59. Otherwise, if test step 58 determines that the time between LastQRSPeak and QRSPeak is not greater than MinSep, then a further test step 60 is performed as depicted in FIG. 9N to determine whether the absolute value "V1" of the second derivative at QRSPeak is greater than its absolute value "V2" at LastQRSPeak. If test step 60 determines that "V1" is not greater than V2, then the loop is repeated commencing with step 41. Otherwise, if test step 60 determines that V1 is greater than V2; or, if test step 57 determines that LastQRSPeak is nil; or, after performance of step 59; step 61 is performed to derive a QRS model from the current QRS candidate as follows:

MaxSep := 2*(QRSPeak−LastQRSPeak), or MaxQRSSep if LastQRSPeak is nil

MinSep := ½*(QRSPeak−LastQRSPeak), or MinQRSSep if LastQRSPeak is nil

MaxWidth := Min(2*(QRSOff−QRSOn), QRSMaxWidth)
MinWidth := Max(½*(QRSOff−QRSOn), QRSMinWidth)
MinHeight := Max(½*(height of QRS), QRSMinHeight)
D2Thresh := ½*(Abs(D2) at QRSPeak)
MinD2Height := ½*(height of QRS in D2)

After performance of QRS model derivation step 61, step 62 is performed to set LastQRSPeak, LastQRSOn, and LastQRSOff equal to the values of QRSPeak, QRSOn, and QRSOff respectively. After performance of step 62, the loop is repeated commencing with step 41.

P and T Wave Detection

The operation of P and T detector 25 will now be described with reference to FIG. 7. As previously mentioned, P and T wave detector 25 applies the FIG. 7 algorithm to the output of QRS detector 22 and to the ECG samples stored in buffer 21 to detect the onsets, peaks, and offsets of the P and T waves in each ECG sample waveform. It is however important to understand that usage of the previously described QRS detector 22 is not essential to the operation of P and T detector 25. The prior art has evolved a variety of QRS detectors, many of which can detect onsets, peaks, and offsets of QRS waves in ECG sample waveforms. Any such QRS detector could readily be adapted and substituted for QRS detector 22 to serve as an input source of onsets, peaks, and offsets of QRS waves for P and T detector 25.

The operation of P and T detector 25 is conveniently characterized in terms of the following definitions:

MinPWidth absolute minimum time between P wave onset and offset

MinPHeight absolute minimum height from onset or offset to peak of P wave

MinTWidth absolute minimum time between T wave onset and offset

MinTHeight absolute minimum height from onset or offset to peak of T wave

Figure 7:
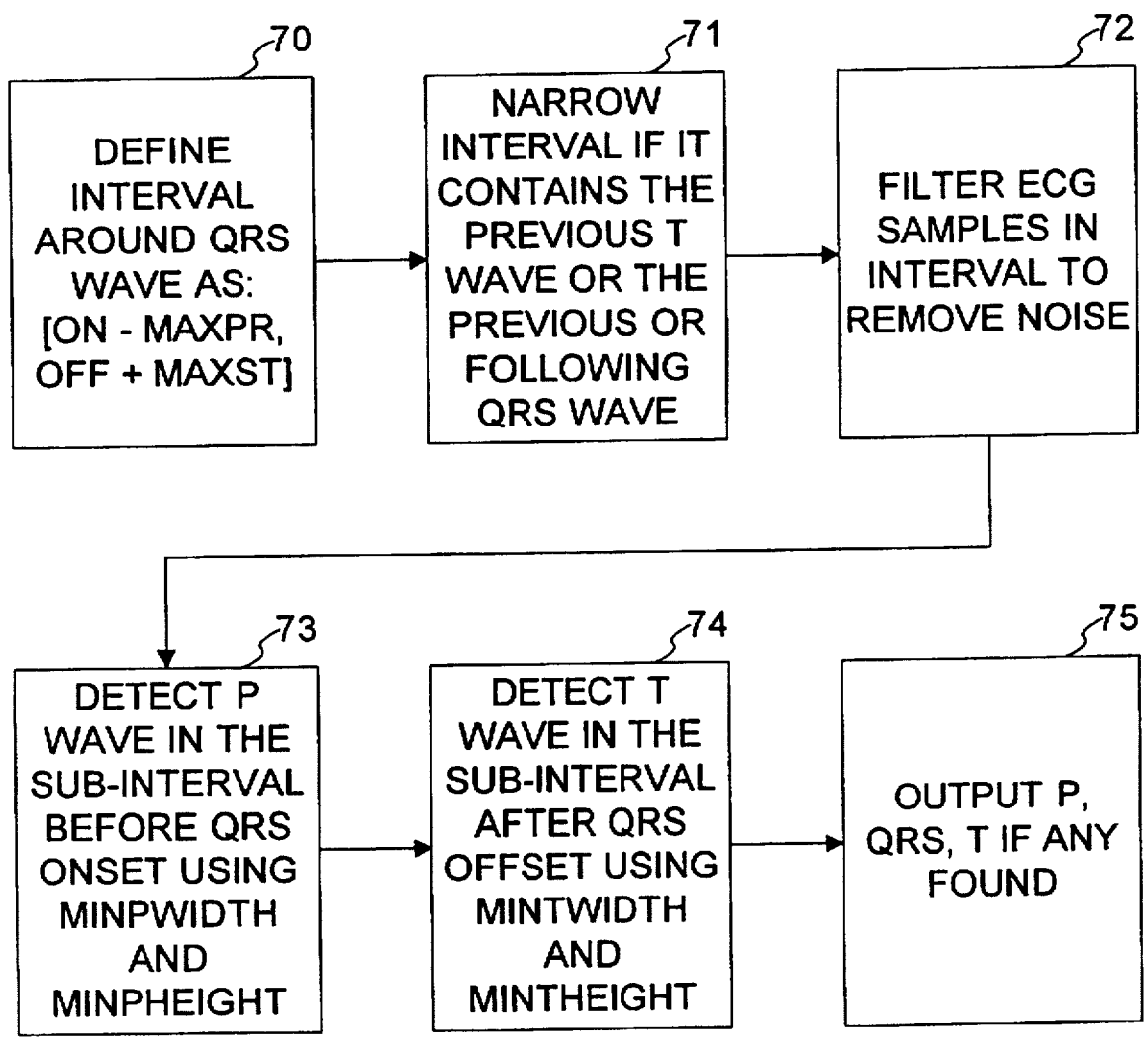
FIG. 7 is a flowchart which depicts the sequence of steps performed in detecting P or T waves in accordance with the invention.

With reference to FIG. 7, step 70 defines a time interval "MaxPR" (FIG. 9O) seconds prior to the onset of the selected input QRS wave; and, a time interval "MaxST" seconds after the offset of the selected input QRS wave. Step 71 narrows the MaxPR interval, as shown in FIG. 9P, so that it does not overlap any previously detected T or QRS wave, and narrows the MaxST interval so that it does not overlap the following QRS wave. Step 72 filters the input ECG samples obtained from buffer 21 to remove noise. As hereinafter described with reference to FIG. 8, step 73 detects, in the narrowed MaxPR interval, the best candidate P wave which satisfies the MinPWidth and MinPHeight thresholds; and, step 74 detects, in the narrowed MaxST interval, the best candidate T wave which satisfies the MinTWidth and MinTHeight thresholds. Step 75 then outputs the P wave detected by step 73, if any; the T wave detected by step 74, if any; and the QRS wave previously detected by QRS detector 22.

Figure 8:
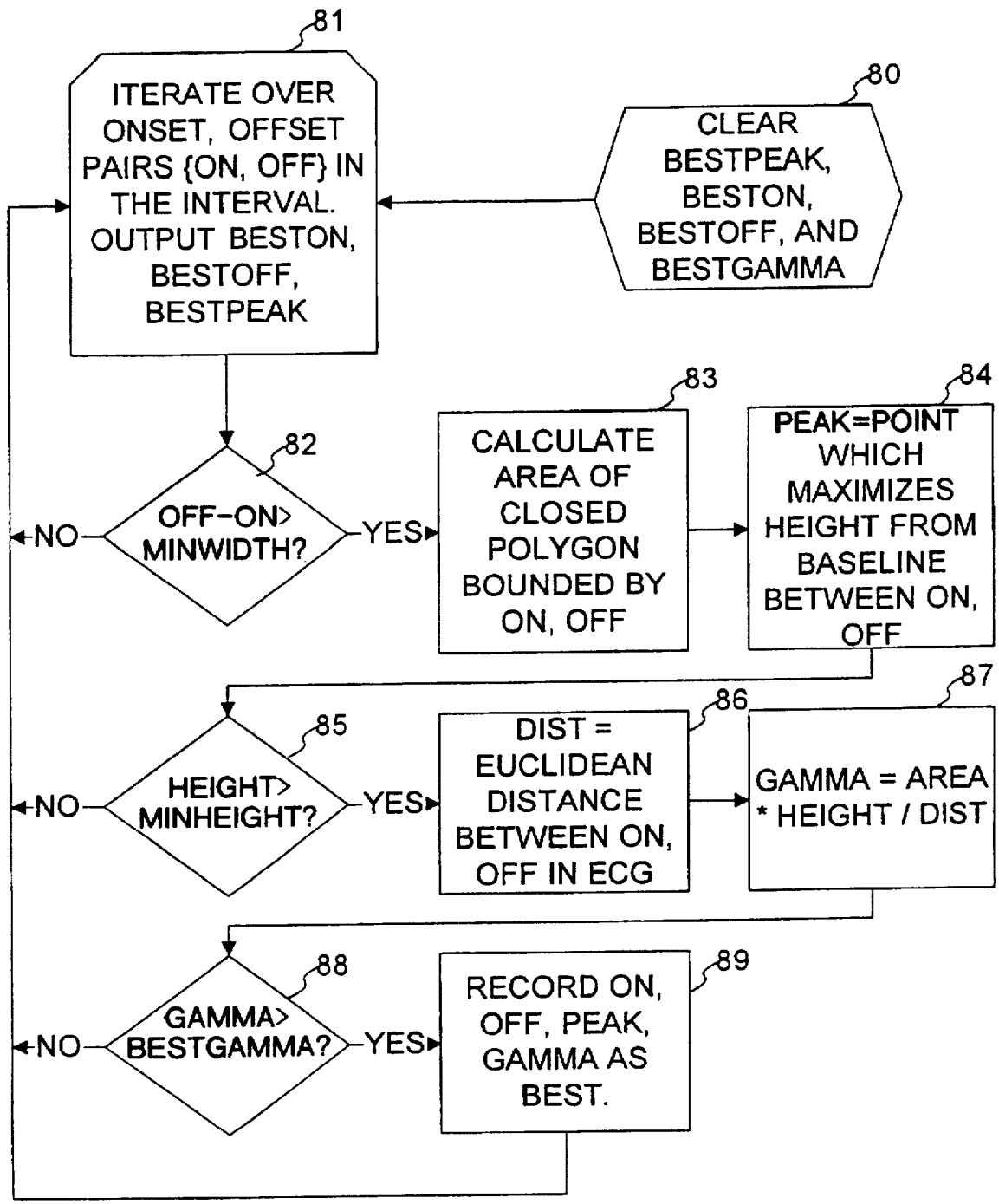
FIG. 8 is a flowchart which depicts the sequence of wave detection sub-steps performed during either P or T wave detection in accordance with the invention.
Figure 9O:
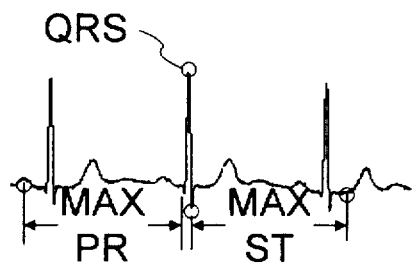
Figure 9P:
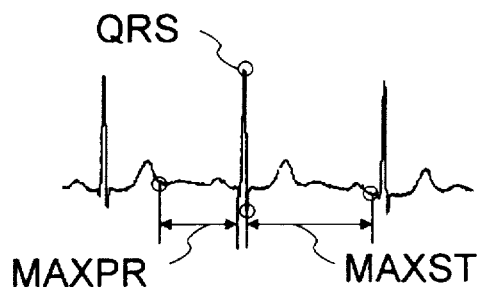

FIG. 8 provides greater detail of the operations performed during steps 73 and 74. The same operations are performed during each of steps 73 and 74, the only difference being that step 73 is performed with respect to the narrowed MaxPR interval to detect the best candidate P wave, and step 74 is performed with respect to the narrowed MaxST interval to detect the best candidate T wave. Accordingly, in the following description, reference is made to the "candidate wave", which those skilled in the art will understand to mean a candidate P wave if the FIG. 8 operations are performed during step 73, and to mean a candidate T wave if the FIG. 8 operations are performed during step 74.

The FIG. 8 operations are conveniently characterized in terms of the following definitions:

MinWidth minimum time between onset and offset of candidate wave

MinHeight minimum height from onset or offset to peak of candidate wave

Figure 9Q:
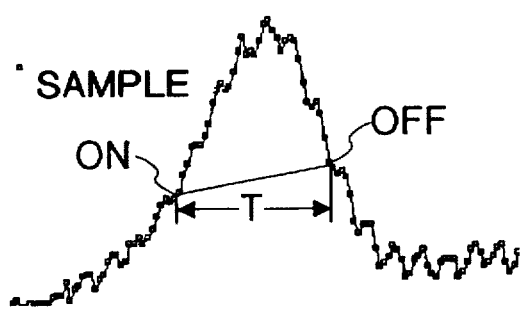

BestPeak location of best candidate wave's peak
BestOn location of best candidate wave's onset
BestOff location of best candidate wave's offset
BestGamma measure of best candidate wave's validity Initialization step 80 sets the values of BestOn, BestOff, BestPeak, and BestGamma to nil, and sets the values of MinWidth and MinHeight to equal parameters passed into P and T detector 25. Step 81 initiates a loop which iteratively evaluates the "On" and "Off" values (FIG. 9Q) for every pair of sample points within the input interval of the candidate wave (i.e. the narrowed MaxPR interval in the case of step 73, or the narrowed MaxST interval in the case of step 74) and selects the BestOn, BestOff, and BestPeak values for the candidate wave.

Figure 9R:
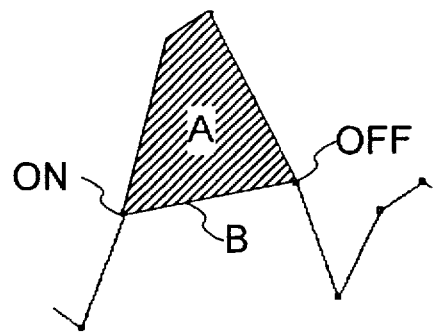

More particularly, a candidate onset value "On", and a candidate offset value "Off" are selected during step 81. Test step 82 then determines whether the time "T" (FIG. 9Q) between the On and Off values is greater than MinWidth. If test step 82 determines that T is not greater than MinWidth then the loop is repeated commencing with step 81. Otherwise, if test step 82 determines that T is greater than MinWidth, then step 83 is performed to determine the area "A" (FIG. 9R) of the closed polygon bounded by all of the sample intervals between and including the On and Off values, the polygon having a base line "B" (FIG. 9R) extending linearly between the On and Off values.

Figure 9S:
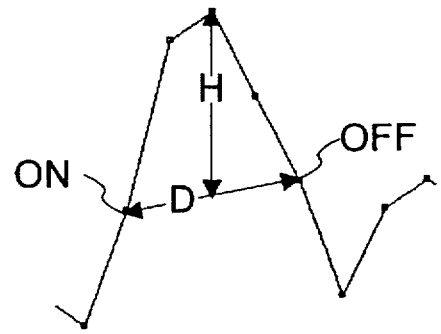

Step 84 then selects as the "Peak" sample (FIG. 9S) the ECG sample which has the maximum height "h" above base line B. In this context, "height" refers to the distance in ECG samples from Peak to base line B. A test step 85 is then performed to determine whether h is greater than MinHeight. If test step 85 determines that h is not greater than MinHeight then the loop is repeated commencing with step 81.

Otherwise, if test step 85 determines that h is greater than MinHeight, step 86 is performed to determine the Euclidean distance "d" (FIG. 9S) between the candidate On and Off values in terms of both ECG samples and time. Step 87 is then performed to determine a candidate value "Gamma"= A*h/d. Test step 88 is then performed to determine whether Gamma is greater than BestGamma. If test step 88 determines that Gamma is not greater than BestGamma then the loop is repeated commencing with step 81. Otherwise, if test step 88 determines that Gamma is greater than BestGamma, then the values of BestOn, BestOff, BestPeak, and BestGamma are replaced with the values of On, Off, Peak, and Gamma and the loop is then repeated commencing with step 81.

Summary

It will thus be understood that the apparatus depicted in FIG. 5 receives input ECG samples, detects QRS waves in such samples, and then detects the P and T waves adjacent each QRS wave. The ECG samples are read from a sequential storage device and buffered in a computer memory. Approximations to the first and second derivatives of the ECG samples are also computed and buffered. The ECG samples and the first and second derivative approximations are input to a QRS detector, which outputs the onsets, offsets and peaks of detected QRS waves.

The QRS detector maintains records of the last detected QRS (which is a provisional candidate for output as a valid QRS wave, until its final acceptance), and a QRS model derived from the last detected QRS. Final acceptance of the last QRS wave as a valid QRS wave depends upon the outcome of tests which involve the next candidate QRS wave. The QRS detector iterates over every ECG sample in the candidate wave, comparing each sample to the QRS model to determine whether the selected sample is the peak of a QRS wave. If no QRS is detected after a maximum expected QRS interval, the model parameters are relaxed and the ECG samples subsequent to the last valid QRS are re-examined. If the model is already fully relaxed, no new QRS is detected and the last detected QRS is accepted as valid and output.

Once an ECG sample is determined to be a candidate QRS peak, the candidate QRS wave's onset and offset are determined by setting thresholds and examining the first and second derivatives near the peak. The candidate peak, onset, and offset must satisfy the QRS model thresholds. If the candidate satisfies the model and is sufficiently far from the previous QRS, the previous QRS is output as a detected QRS wave. If the candidate satisfies the model but is too close to the previous QRS, the QRS having the lesser second derivative value at its peak is rejected. If the current candidate passes all tests, the last QRS is accepted as valid and output, and the current QRS candidate is recorded as the last QRS.

Once a QRS has been detected (either by QRS detector 25 or by a suitable substitute QRS detector), a P and T wave detector looks for a P wave preceding the QRS wave and for a T wave following it. These waves are found by finding waves in the ECG samples which satisfy minimum height and width requirements and lie near the QRS. The ECG samples in these ranges are first filtered to remove noise. The onset and offset of the P and T waves are chosen according to their height relative to their onset and offset, the distance between their onset and offset, and the area of a closed polygon bounded by the ECG samples between their onset and offset. The P and T wave detector outputs include the onset, offset, and peaks of the P and T waves.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A method of detecting P and T waves in an electrocardiogram signal containing said P and T waves and containing previously detected QRS waves, said method comprising the steps of:

a. selecting a next one of said previously detected QRS waves;

b. defining a first time interval within said electrocardiogram signal, said first time interval preceding said selected QRS wave and containing a plurality of samples of said electrocardiogram signal;

c. defining a second time interval within said electrocardiogram signal, said second time interval following said selected QRS wave and containing a plurality of samples of said electrocardiogram signal;

d. narrowing said first time interval to exclude QRS and previously detected T waves preceding said selected QRS wave;

e. narrowing said second time interval to exclude QRS waves following said selected QRS wave;

f. for each pair of said samples in said first time interval:

i. proceeding to step 1(f)(iv) if said pair of samples are separated by a time duration which does not exceed a predefined time duration;

ii. deriving the area, width, and height of a closed polygon having vertices defined by all samples within said first time interval between and including said pair of samples;

iii. deriving a rating for said polygon as a function of said area, width and height;

iv. selecting another pair of said samples and proceeding to step 1(f)(i);

g. selecting as said P wave that one of said step 1(f) (iii) polygons for which said rating is maximal;

h. for each pair of said samples in said second time interval:

i. proceeding to step 1(h)(iv) if said pair of samples are separated by a time duration which does not exceed a predefined time duration;

ii. deriving the area, width, and height of a closed polygon having vertices defined by all samples within said second time interval between and including said pair of samples;

iii. deriving a rating for said polygon as a function of said area, width and height;

iv. selecting another pair of said samples and proceeding to step 1(h)(i); and, i. selecting as said T wave that one of said step 1(h) (iii) polygons for which said rating is maximal.

2. A method as defined in claim 1, further comprising, before said step 1(f), the further step of filtering those portions of said electrocardiogram signal containing said first and second time intervals to remove noise.

3. A method as defined in claim 1, wherein said previously detected QRS waves are respectively characterized by onset, offset and peak values, said method further comprising detecting said onset, offset and peak values by:

a. deriving first and second derivative approximations of said electrocardiogram signal;

b. deriving from said previously detected QRS waves a plurality of threshold values which collectively characterize acceptable bounds for said onset, offset and peak values;

c. for each of said previously detected QRS waves, selecting candidate values for said onset, offset and peak values;

d. comparing said candidate values to said threshold values to derive a measure of difference therebetween;

e. accepting said candidate values as said onset, offset and peak values respectively if said difference does not exceed a predefined minimum;

f. if said difference exceeds said predefined minimum, increasing said respective threshold values and proceeding to said step 3(c).

4. A method as defined in claim 1, wherein said steps 1(f)(ii) and 1(h)r(ii) each further comprise:

a. deriving said closed polygon area as that area bounded by all of said samples between and including said pair of samples, said polygon having a base line extending linearly a distance "d" between said pair of samples;

b. deriving a maxim um vertical displacement "h" between said base line and any portion of said polygon above said base line; and, c. comparing said maximum vertical displacement to a predefined minimum vertical displacement; and, d. if said maximum vertical displacement exceeds said predefined minimum vertical displacement then defining said rating=A*h/d for said pair of samples.

5. A method as defined in claim 1, wherein:
   a. said narrowing step 1(d) further comprises:
      i. if said first time interval overlaps a time interval occupied by a previously detected T wave portion of said electrocardiogram signal preceding said first time interval, reducing said first time interval to exclude said previously detected T wave portion;
      ii. if said first time interval overlaps a time interval occupied by a previously detected QRS wave portion of said electrocardiogram signal preceding said first time interval, reducing said first time interval to exclude said previously detected QRS wave portion; and,
   b. said narrowing step 1(e) further comprises:
      i. if said second time interval overlaps a time interval occupied by a previously detected QRS wave portion of said electrocardiogram signal following said second time interval, reducing said second time interval to exclude said previously detected QRS wave portion.

6. A method as defined in claim 1, wherein said previously detected QRS waves are detected by, for each pair of samples within said respective first and second time intervals:
   a. deriving first and second derivative approximations of said electrocardiogram signal;
   b. comparing said second derivative approximations and selecting as a first peak that one of said samples for which said second derivative approximation is greatest;
   c. proceeding to step 6(q) if said first peak second derivative approximation does not exceed a predefined minimum second derivative approximation value;
   d. comparing said second derivative approximations for said samples immediately preceding said first peak and selecting as a second peak that one of said preceding samples for which said second derivative approximation is greatest;
   e. comparing said second derivative approximations for said samples immediately following said first peak and selecting as a third peak that one of said following samples for which said second derivative approximation is greatest;
   f. proceeding to step 6(q) if said second and third peaks are separated by a time duration which exceeds a predefined maximum onset-offset time duration;
   g. proceeding to step 6(q) if the difference between said first and second peak second derivative approximations does not exceed a predefined minimum peak separation value or if the difference between said first and third peak second derivative approximations does not exceed said predefined minimum peak separation value;
   h. defining a first threshold D1L as a function of said first derivative approximations for said samples between said first and second peaks;
   i. defining a second threshold D1R as a function of said first derivative approximations for said samples between said first and third peaks;
   j. defining a third threshold D2LR as a function of said second derivative approximations for said samples between said first and third peaks;
   k. selecting as a QRSOn value that one of said samples for which said first and second derivative approximations respectively do not exceed said D1L and D2LR thresholds;
   l. selecting as a QRSOff value that one of said samples for which said first and second derivative approximations respectively do not exceed said D1R and D2LR thresholds;
   m. proceeding to step 6(q) if said selected QRSOn and QRSOff values are separated by a time duration which does not exceed a predefined QRS time duration;
   n. if said selected QRSOn and QRSOff values are separated by a time duration which exceeds said predefined QRS time duration then selecting said second peak as said QRSOn value and selecting said third peak as said QRSOff value;
   o. proceeding to step 6(q) if the average values of:
      i. said samples between said first peak and said QRSOn value;
      ii. said samples between said first peak and said QRSOff value;
      do not exceed a predefined average value;
   p. if said first peak is not separated from said first peak of an immediately preceding, previously detected QRS wave then rejecting that one of said samples for which said second derivative approximation is lowest; and,
   q. selecting a next pair of said samples and repeating steps 6(a) through 6(p) until none of said samples remain.

* * * * *